(12) United States Patent
Chouinard

(10) Patent No.: US 7,438,712 B2
(45) Date of Patent: Oct. 21, 2008

(54) MULTI-BRAID EXTERIOR TUBE

(75) Inventor: Paul Chouinard, Maple Grove, MN (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 10/379,932

(22) Filed: Mar. 5, 2003

(65) Prior Publication Data

US 2004/0176740 A1 Sep. 9, 2004

(51) Int. Cl.
*A61M 25/00* (2006.01)
(52) U.S. Cl. ....................................... 604/527
(58) Field of Classification Search .......... 604/523–528
See application file for complete search history.

(56) References Cited

U.S. PATENT DOCUMENTS

| | | | |
|---|---|---|---|
| 4,531,943 A | 7/1985 | Van Tassel et al. | |
| 4,817,613 A | * 4/1989 | Jaraczewski et al. | ......... 600/435 |
| 5,037,404 A | 8/1991 | Gold et al. | |
| 5,069,674 A | 12/1991 | Fearnot et al. | |
| 5,176,661 A | 1/1993 | Evard et al. | |
| 5,180,376 A | 1/1993 | Fischell | |
| 5,234,416 A | * 8/1993 | Macaulay et al. | ........... 604/527 |
| 5,279,596 A | 1/1994 | Castaneda et al. | |
| 5,312,356 A | 5/1994 | Engelson et al. | |
| 5,318,032 A | 6/1994 | Lonsbury et al. | |
| 5,496,294 A | 3/1996 | Hergenrother et al. | |
| 5,531,715 A | 7/1996 | Engelson et al. | |
| 5,531,721 A | 7/1996 | Pepin et al. | |
| 5,538,512 A | 7/1996 | Zenzon et al. | |
| 5,554,139 A | 9/1996 | Okajima | |
| 5,569,220 A | 10/1996 | Webster, Jr. | |
| 5,599,325 A | 2/1997 | Ju et al. | |
| 5,603,698 A | 2/1997 | Roberts et al. | |
| 5,605,543 A | 2/1997 | Swanson | |
| 5,674,208 A | 10/1997 | Berg et al. | |
| 5,700,269 A | 12/1997 | Pinchuk et al. | |
| 5,702,373 A | 12/1997 | Samson | |
| 5,702,418 A | 12/1997 | Ravenscroft | |
| 5,707,376 A | 1/1998 | Kavteladze et al. | |
| 5,713,851 A | 2/1998 | Boudewijn et al. | |
| 5,735,859 A | 4/1998 | Fischell et al. | |
| 5,755,708 A | 5/1998 | Segal | |
| 5,769,830 A | 6/1998 | Parker | |
| 5,772,669 A | 6/1998 | Vrba | |
| 5,776,141 A | 7/1998 | Klein et al. | |
| 5,836,926 A | 11/1998 | Peterson et al. | |
| 5,871,537 A | 2/1999 | Holman et al. | |
| 5,957,974 A | 9/1999 | Thompson et al. | |

(Continued)

FOREIGN PATENT DOCUMENTS

EP  1068876 A2  1/2001

(Continued)

*Primary Examiner*—Kevin C. Simrons
*Assistant Examiner*—Catherine N Witczak
(74) *Attorney, Agent, or Firm*—Hoffman & Baron, LLP

(57) ABSTRACT

A multiple braid exterior tube having a composite structure which includes an inner tubular layer, reinforcing layers and a polymer matrix layer. The exterior tube is formed with polymeric materials and metallic reinforcing braiding configured to provide greater tensile strength and stiffness. The exterior tube is used for a variety of medical devices such as a sheath component for intravascular devices and catheters.

11 Claims, 3 Drawing Sheets

U.S. PATENT DOCUMENTS

| | | | |
|---|---|---|---|
| 5,980,533 A | 11/1999 | Holman | |
| 5,984,964 A | 11/1999 | Roberts et al. | |
| 6,019,778 A | 2/2000 | Wilson et al. | |
| 6,042,578 A | 3/2000 | Dinh et al. | |
| 6,126,685 A | 10/2000 | Lenker et al. | |
| 6,217,566 B1 | 4/2001 | Ju et al. | |
| 6,287,329 B1 | 9/2001 | Duerig et al. | |
| 6,290,692 B1 * | 9/2001 | Klima et al. | 604/524 |
| 6,355,060 B1 | 3/2002 | Lenker et al. | |
| 6,368,344 B1 | 4/2002 | Fitz | |
| 6,425,898 B1 | 7/2002 | Wilson et al. | |
| 6,443,979 B1 | 9/2002 | Stalker et al. | |
| 6,503,353 B1 | 1/2003 | Peterson et al. | |
| 6,520,983 B1 | 2/2003 | Colgan et al. | |
| 6,652,692 B2 * | 11/2003 | Pedersen et al. | 156/143 |

FOREIGN PATENT DOCUMENTS

| EP | 1068876 | * | 5/2001 |
|---|---|---|---|

* cited by examiner

MULTI-BRAID EXTERIOR TUBE

BACKGROUND OF THE INVENTION

I. Field of the Invention

The present invention relates to multi-braided exterior tubes having a lubricious inner layer, reinforcing layers and polymeric matrix layer. The present invention is used for a variety of medical devices such as intravascular devices, and catheters, such as guide catheters, angioplasty catheters, stent delivery devices, angiographic catheters, neuro catheters, and the like.

II. Discussion of the Prior Art

Tubes have been used for a variety of medical devices. Tubes have been used as a sheath component for catheters or exterior tubes for delivery devices. Several types of catheters having a sheath component are utilized for intravascular treatment. Examples of intravascular catheters include guide catheters, angioplasty catheters, stent delivery devices, angiographic catheters, neuro catheters, and the like.

Guiding catheters typically have preformed bends formed along their distal portion to facilitate placement of the distal end of the guiding catheter into the ostium of a particular coronary artery of a patient. In order to function efficiently, guiding catheters should have a relatively stiff yet flexible main body portion. The stiff main body portion gives the guiding catheter greater longitudinal stiffness which provides sufficient "pushability" to allow the guiding catheter to be inserted percutaneously into a peripheral artery, moved and rotated in the vasculature to position the distal end of the catheter at the desired site adjacent to a particular coronary artery. However, it has sufficient bending flexibility so that it can track over a guidewire and be maneuvered through a tortuous path to the treatment site. In addition, a soft distal tip at the very distal end of the catheter may be used to minimize the risk of causing trauma to a blood vessel while the guiding catheter is being moved through the vasculature to the proper position. Such a soft tip is described in U.S. Pat. No. 4,531,943. In addition, the inner surface of the guiding catheter should be lubricious to facilitate movement of guidewires, balloon catheters and other interventional medical devices therethrough.

In that the path taken by intravascular catheters is sometimes tortuous, it is important that an intravascular catheter provide torsional stiffness so that the torque be transmitted to the distal end in a smooth, controllable fashion. Moreover, the catheter should have sufficient longitudinal strength so as not to kink or fold as it is advanced or withdrawn through the vascular system. It should also possess a lubricious core lumen to facilitate passage of a guidewire or possibly another catheter or device therethrough.

Intravascular catheters may also be used as an outer sheath or exterior tube for a stent or stent-graft delivery device. In this application the outer sheath needs to provide sufficient bending flexibility to allow the device to be tracked through the anatomy as well as longitudinal stiffness to provide pushability and to minimize elongation. In the case of a self-expanding stent, the outer sheath must maintain the stent-graft in the compressed state. The stent exerts outward force against the inside of the outer sheath. Over time, the stent can form impressions in the inner surface of the sheath. During deployment a tensile deployment force is applied to the outer sheath to overcome the frictional forces between the stent and the inside of the outer sheath further causing the outer sheath to longitudinally deform. Typically, longer stents result in a higher deployment force, and a more extensive stretching of the exterior tube. Eventually, a threshold is reached where the outer sheath is not capable of sustaining the tensile loads without sustaining permanent deformation. When this threshold is reached, this typically results in an inability to deploy the stent. Thus, the lengths of the stents or stent-grafts that are offered on a particular delivery system can be limited by the tensile strength or stiffness of an outer sheath of the delivery system.

A braided reinforcement layer incorporated into an outer sheath provides greater longitudinal tensile strength, compressive stiffness and longitudinal stiffness, yet the braid structure provides flexibility as needed for the intravascular environment in which it is used. But the reinforcement layer must also not add significant thickness to the diameter of the catheter which must be easily maneuverable within the vascular system. It is advantageous to have catheters or delivery systems which are as small as possible to reach into smaller vessels, and cause less trauma to the patient. Some attempts have been made to offer the advantages of one reinforcing layer such as those found in U.S. Pat. No. 6,019,778 to Wilson et al., U.S. Pat. No. 5,836,926 to Peterson, et al., and U.S. Pat. No. 6,042,578 to Dinh et al. all of which are incorporated herein. However, none of these patent have suggested using more than one layer of reinforcement.

It is also a desirable feature of certain intravascular catheters that it possesses a relatively large lumen to maximize the available volume available for implantable components or fluids, such as radiopaque contrast fluid to be injected therethrough and out the distal end so that the area of the vascular system under investigation can be viewed fluoroscopically.

A desirable sheath for the above-mentioned utility has a relatively small O.D. and a relatively large I.D. which dictates a relatively thin wall. Further the outer sheath must provide the desired longitudinal stiffness providing adequate "pushability" and tensile strength characteristics, and radial torsional stiffness, to allow for placement of the device in the narrow, tortuous environment of the intravascular system without injury to the patient. The outer sheath must provide a balance between increased longitudinal stiffness and bending flexibility to provide strength yet flexibility for movement within a body lumen.

SUMMARY OF THE INVENTION

The present invention provides a sheath component of an intraluminal delivery system which may be used in various applications, especially vascular applications. The sheath of the present invention includes a inner tubular layer, at least two braided layers and an outer polymeric matrix layer. The inner tubular layer forms a polymeric luminal surface. The braided layers are disposed about the inner tubular layer and the polymeric matrix layer may encapsulate at least two of the braided layers and joins the braided layers to the inner tubular layer.

The inner tubular layer may be selected from a group of materials including fluoropolymers, such as polytetrafluoroethylene, polyesters, polyurethanes, polyolefins, polymethylacetates, copolymers and combinations thereof. The inner tubular layer may provide a polymeric luminal surface which provides a lubricous surface.

The braided layers may include individual fibers or wires at each layer. The fibers at each layer may be cross-braided at different angles such that each layer has a different angle of cross-braiding. The braided layer may include at least two braided layers, such as first and second braided layer. The first braided layer has individual fibers or wires cross-braided at a first angle. The second braided layer has individual threads or wires cross-braided at a second angle. The first angle is preferably greater or less than the second angle.

The present invention further provides a sheath component of an intraluminal delivery system that may include an elongated tubular member. The tubular member may include an inner layer, a first-braid layer disposed about the inner layer and a second braid layer disposed about the first braid layer. A polymeric matrix layer may join together the inner layer, the first braid layer and the second braid layer.

The present invention still further provides a delivery system for delivering an intraluminal device including a tubular endoluminal prosthesis and a deployment device. The tubular prosthesis has a luminal surface and an opposed exterior surface. The deployment device includes an elongated outer sheath for maintaining the prosthesis in an unexpanded condition during delivery of the prosthesis to the desired site. The outer sheath is retractable with respect to the prosthesis and includes an inner tubular layer, a first braid layer, a second braid layer and a polymeric matrix layer. The first braid layer is disposed about the inner tubular layer and the second braid layer is disposed about the first braid layer. The polymeric matrix layer may join together the inner tubular layer, the first braid layer and the second braid layer.

Additionally, the present invention provides a method of making an elongated tubular member of an intraluminal deployment device. The method of the present invention includes providing components of an inner tubular layer, a first braid layer, a second braid layer, and a polymeric matrix layer; disposing the first braid layer about the inner tubular layer; disposing the second braid layer about the first braid layer; disposing the polymer matrix layer about the second braid layer; and integrally joining each of said layers to form said tubular member.

The sheath component of the present invention is designed to take advantage of the inherent beneficial properties of the materials forming each of the layers. The inner tubular layer provides a luminal surface for reduced friction in contact with the interior device. The braided layers provide the tensile strength and stiffness desired for pushablilty and flexibility in guiding the sheath through a body lumen. The polymeric matrix provides the beneficial properties of encapsulating the braid layers to prevent abrasion and a frictional injury against the body lumen as the sheath is guided therethrough. The polymeric matrix layer provides joining the braided layers and the inner tubular layers together.

DETAILED DESCRIPTION OF THE INVENTION

Figure 2:
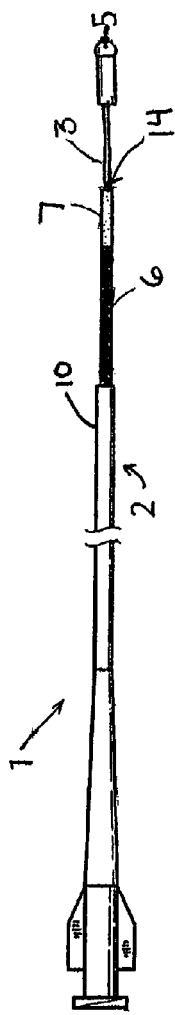
FIG. 2 is a cutaway schematic illustration of a delivery system of the present invention having the composite outer sheath and a portion thereof removed to show the various layers of the outer sheath including inner tubular layer, braided layers, and polymeric matrix layer; and shaft.

The present invention is a composite sheath component of an intraluminal delivery system 1 for delivering a stent or stent-graft 4 to an intended fixation site or treatment site within a body lumen, then controllably releasing the stent-graft for radial self-expansion and fixation within the lumen. The composite outer sheath 2 includes a multi-layer structure with circumferential braided layers 6 interposed between an inner tubular layer 7 and a polymeric matrix layer 10.

Figure 1:
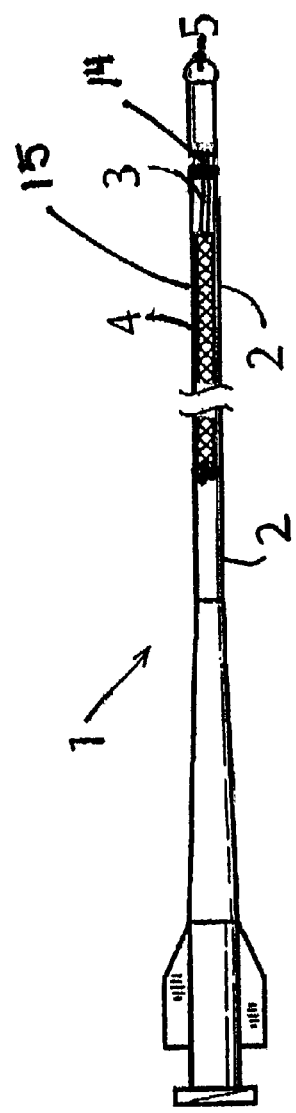
FIG. 1 is a cutaway schematic illustration of a loaded delivery system having the composite outer sheath, cut out to show the internal features, according to the present invention.

As shown in FIG. 1, a delivery system 1 includes an outer sheath 2 and an inner shaft 3. The outer sheath 2 can have any desired inner and outer diameter depending on the application. Typical dimensions are an inner diameter of between about 0.127 cm to about 0.680 cm., and an outer diameter of about 0.1470 cm. to about 0.70 cm. The thickness of the outer sheath 2 can range from about 0.01 cm. to about 0.10 cm. depending on the application. A central lumen 14 runs the length of sheath 2. A distal end region 15 of the outer sheath 2 surrounds stent-graft 4. An inner shaft 3 is contained within lumen 14 and runs along the entire length of the outer sheath 2. At the distal end of inner shaft 3 is a tapered distal tip 5 which extends beyond the outer sheath 2. Stent-graft 4 surrounds inner shaft 3, confined between the inner shaft 3 and outer sheath 2. The inner shaft can have a lumen to accommodate a flexible guidewire (not shown).

The stent-graft 4 is formed of resilient materials, and in FIG. 1 is shown elastically compressed into a radially-reduced and axially-elongated delivery state. Outer sheath 2 maintains the stent-graft 4 in the delivery state against its elastic restoring force. A stopper (not shown) is mounted to the inner shaft 3 and occupies the space between the inner shaft 3 and the outer sheath 2. As the outer sheath 2 is moved proximally to the inner shaft 3 the stopper prevents the stent-graft 4 from following the outer sheath 2 as it reacts proximal to stent-graft 4.

Outer sheath 2, while maintaining stent-graft 4 in the delivery configuration, is moved transluminally to deliver the stent-graft 4 to the treatment site. Once the stent-graft is positioned as intended, the inner shaft 3 remains stationary while the outer sheath 2 is withdrawn proximally. The stent-graft 4 progressively radially self-expands toward an intimate contact with tissue at the treatment site.

When a stent-graft 4 is deployed using a typical coaxial catheter deployment mechanism, as described, a tensile deployment force is applied to the outer sheath 2 to overcome the frictional forces between the stent and the inside of the outer sheath 2. The tensile force applied to the outer sheath 2 causes the outer sheath 2 to stretch. Typically, longer stents result in a higher deployment force, and a more extensive stretching of the exterior tube. Eventually, a threshold is reached where the exterior tube is not capable of sustaining the tensile loads without sustaining permanent deformation. When this threshold is reached, this typically results in an inability to deploy the stent. Thus, the lengths of the stents or stent-grafts that are offered on a particular delivery system can be limited by the tensile strength and stiffness of an outer sheath.

The present invention provides a delivery system 1 with an outer sheath 2 having increased tensile strength thereby raising the tensile threshold of the device. In addition, the outer sheath 2 provides greater longitudinal stiffness to facilitate advancement of the device and deployment of the stent without incurring deformation. As shown in FIG. 2 is the delivery system 1 having a composite outer sheath 2 of the present invention and a portion thereof removed to show the layers of the outer sheath 2. The outer sheath 2 includes an inner tubular layer 7, braided layers 6, and an outer polymeric matrix layer 10 joining the braided layers 6 to the inner tubular layer 7.

i. Inner Tubular Layer

Figure 6:
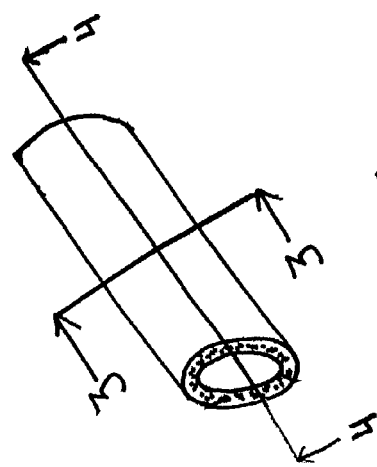
FIG. 6 shows perspective view of multi-braided exterior sheath according to the present invention.
Figure 3:
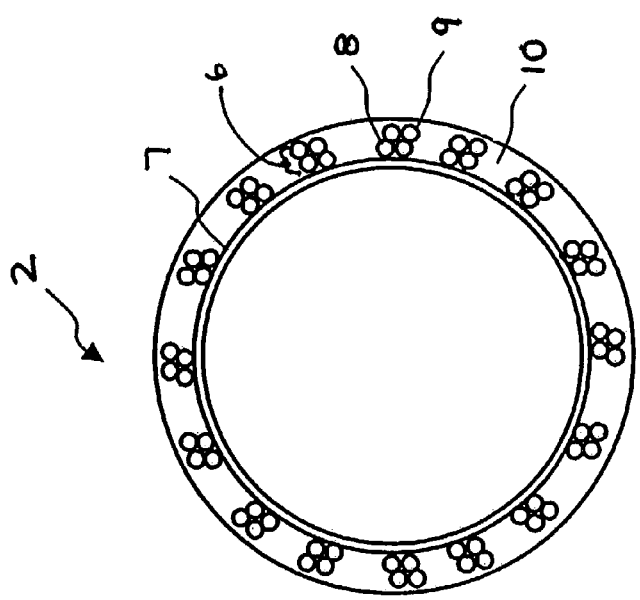
FIG. 3 is a cross-sectional view of a double braided outer sheath of FIG. 6 taken across the 3-3 axis according to the present invention.
Figure 4:
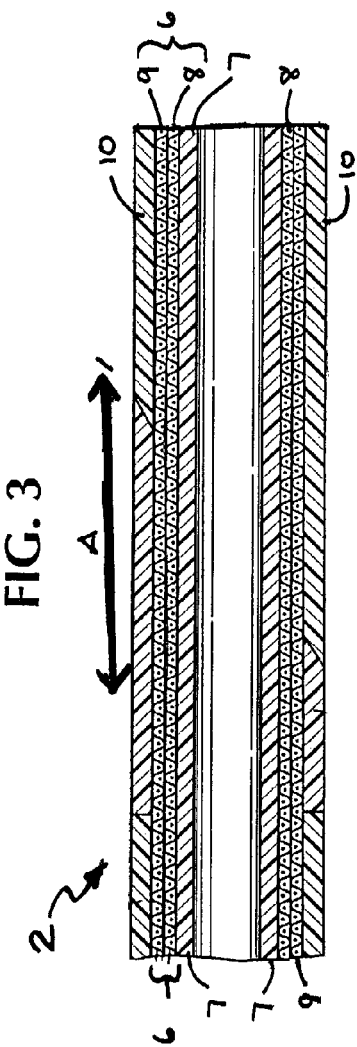
FIG. 4 is a longitudinal sectional view of the outer sheath of FIG. 6 taken across the 4-4 axis according to the present invention.

As shown in FIGS. 3, 4 and 6, the inner tubular layer 7 may be a continuous tubular structure which forms a polymeric luminal surface which provides a lubricous surface for allowing the delivery of inner material and devices, such as a stent-graft. Inner layer 7 provides a low coefficient of friction surface to reduce the forces required to deploy the stent-graft 4. The inner layer 7 is formed by various methods such as by forming a tube with a sheet, a spirally wrapped strip or extruding a tube. For example, if a sheet is used, the inner layer 7 can be formed by wrapping the sheet around a longitudinal axis, such as around a mandrel (not shown), to form a tubular body with a longitudinal seam. Continuous, as used herein, refers to a tubular structure whose surface extends substantially uninterrupted throughout the longitudinal length thereof. In the case of an extruded tube, the tubular structure is completely uninterrupted. A substantially uninterrupted tubular structure exhibits enhanced strength and lubricious properties when used as an outer sheath 2. Furthermore, the inner layer 7 may consist of one single layer or it may consist of multiple layers of a polymer sheet around the longitudinal axial to create a multi-layer inner tube. Suitable materials for the inner tubular layer include polymers and any suitable material known to those skilled in the art including fluoropolymers, such as polytetrafluoroethylene (PTFE), polyesters, polyurethanes, polypropylenes, polyolefins, polyvinyls, polymethylacetates, polyethylene, polyamide and combinations thereof.

ii. Outer Polymeric Matrix Layer

Outer sheath 2 can incorporate a single outer polymeric matrix layer 10 or a plurality of different fused layers to bond the exterior surface of the outer sheath. The varying material can effectively enhance the catheter performance as it is pushed over the guidewire (not shown) through the vascular anatomy. The flexibility of the sheath 2 can improve the manner in which the delivery system 1 tracks over through the body lumen. As shown in FIG. 3, the outer polymeric matrix layer 10 joins together the inner tubular layer 7 and the various braided layers 6, such as first braid layer 8 and second braid layer 9. The inner layer 7 may be bonded to the outer polymeric matrix 10 through spaces in the open wall of the braided layers. The bonding may be effectuated with the use of an adhesive, or by adhering the layers together without an adhesive. Bonding of the PTFE layers without an adhesive may take place by such methods as thermally bonding, also known as laminating. Furthermore, the braided layers 6 may be adhered to the inner layer 7, the outer polymeric matrix layer 10, or both. Similarly, such adherence may take place with or without the use of an adhesive. The components may be fully or partially bonded. The outer layer 10 may come in a variety of different forms depending on the material used. The outer layer 10 may be a liquid material which is sprayed, brushed or dip coated onto the outer sheath 2. The outer layer 10 may also be an extruded layer which is wrapped around the outer sheath and heated to conform to the outer sheath structure. The desired material used for the outer layer 10 provides biocompatible material with high tear and tensile strength, low moisture absorption, flexural fatigue resistance, and thermal stability.

Standard measurements of the hardness of various substances are currently performed using durometer hardness test procedures, such as those set forth in ASTM D2240 herein incorporated by reference. The durometer hardness procedures are used for determining indentation hardness of various substances, and are particularly useful for elastomeric materials. These test methods measure the depression force of a specific type of indentor as it is forced under specific conditions against the material's surface. Due to the various parameters which influence hardness determinations, different durometer scales have been established. A particular scale is chosen depending on the type of material to be measured. The indentor descends at a controlled rate against the specimen surface and a reading is recorded within a specified time period. This procedure is repeated multiple times at different positions on the specimen and the arithmetic mean of the results yields the Shore A measurement.

Durometer scales which are used for durometer hardness measurements include Shore A, B, C, D, DO, O, OO, and M. Each of theses scales has units from 0 to 100. There is no overlap between the scales, although certain materials may be suitable for testing on both scales. The geometry of the indentor and calibrated spring force scales influence the measurements, such that no simple relationship exists between the measurements obtained between different types of durometers. For example, the test for Shore D, which is designed for harder materials than Shore A, is distinct from Shore A in that the indentor is shaped with a pointed tip and the calibrated spring force has a higher force scale then Shore A.

The Shore D hardness for the outer polymeric matrix layer of this invention can range from a Shore D hardness of about 42 to about 80 depending on the number of layers and the desired softness of the sheath. A plurality of outer matrix layers having different durometer values may be fused together to offer a softer outer matrix layer. Suitable material include thermoplastic elastomers, such as copolyesters (COPE's) such as copolyester-ester, copolyether-esters, copolymer with alternately repeating butylene terapthalate hard segments and poly(alkylene oxide), such as polytetramethyleneoxide, soft segments; fluoropolymers, polyurethanes, polyolefins, polyvinyls, polymethylacetates, polyethylene such as polyethylene terephthalate (PET), polyamide, PET, and combinations thereof. An example of suitable commercially available thermoplastics include polyether ester materials such as 74D Arnitel, Arnitel EL740, Arnitel E resin, and Arnitel P resin from Quadrant Engineering Plastics, Reading, Pa.

iii. Braided Layers

As shown in FIG. 4, positioned between outer and inner layers 10 and 7, respectively, is braided layers 6 which include first braid layer 8 and second braid layer 9, which reinforces the sheath 2. The braided layers 6 provides inner layer 7 creating sufficient resistance to the outward radial force of stent 4 within the outer sheath 2 to prevent the stent-graft 4 from becoming imbedded into the outer sheath 2, prior to and during stent deployment. In addition, braided layers 6 provides the sheath greater longitudinal stiffness, the ability to transmit a force applied by the physician at a proximal location, which aids in navigation across tight stenotic lesions within the vascular anatomy and with deployment of the device. Braided layers 6 also gives the outer sheath 2 better resistance to deformation, such as elongation and necking, as a result of tensile loading during sheath retraction for stent-graft deployment. The configuration and number of braided layers 6 can be changed to adjust the torsional stiffness and longitudinal stiffness. This is achieved by changing the pitch of each braid or braid angles; the braid configuration such as 1-over-1, 2-over-1, 2-over-2, 3-over-1, 3-over-2, and etc.; the shape of the individual braidwires, such as round, flat, square; the number of structural strands forming the braid layer; the braid wire diameter; and the number of braided layers.

Figure 5A:
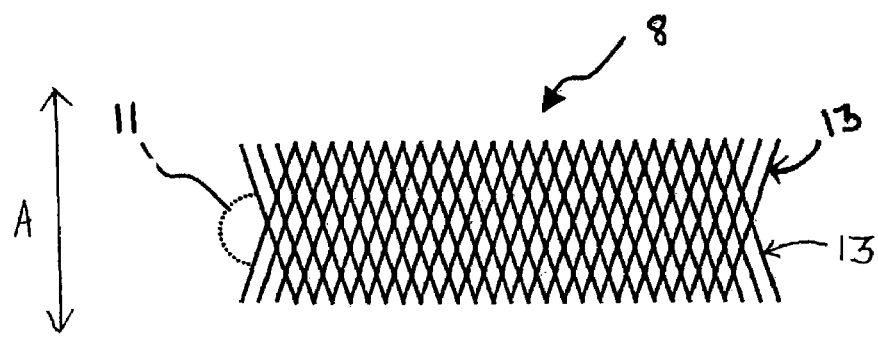
FIGS. 5a-5b show alternative angles of braiding according to the present invention.
Figure 5B:
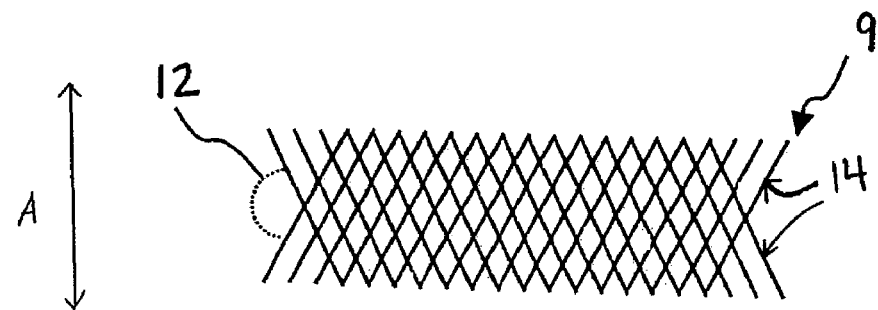

As shown in FIGS. 5a and 5b, a first braid layer 8 of the outer sheath 2 has such crossing wire strands 13 which define a first angle 11 to each other. A second braid layer 9 of the outer sheath 2 has crossing wire strands 14 of the sheath which define at least one second angle 12 to each other. The second angle 12 is different from the first angle 11, with the result that the physical characteristics of the first and second layers are different. Particularly, in this circumstance the torsional and longitudinal rigidity of the respective layers will vary. Furthermore, a sheath constructed in this fashion will have more longitudinal strength and stiffness than a sheath constructed with one braided layer.

Preferably, at least one second angle 12 of crossing strands 14 of a second layer 9 is at least 10 to about 100 degrees, preferably 20 to 70 degrees different from the first angle 11 of the first layer 8, more preferably about 20 to about 40 degrees difference. If desired, a plurality of layers may be present, the layers defining strands having different braid angles from each other.

As shown in FIGS. 5a and 5b, the braided layers are formed of monofilament or multifilament structural strands 13. Strands diameters may range from about 0.002 to 0.015 cm. In general, strands 13 and 14 are arranged in a set of helices wound in opposite directions about a common longitudinal axis A, as also shown in FIG. 4. Strands 13 intersect one another to define rhomboid interstices and a braid angle. Braid angles 11 and 12 are in the range of about 70 to 170 degrees, and more preferably 100 to 150 degrees. The number of structural strands 13 forming a braided layer typically range from 8 to 48, but it can be appreciated that more or less strands may be used depending on the braid angle, size of the sheath and its application.

Figure 5C:
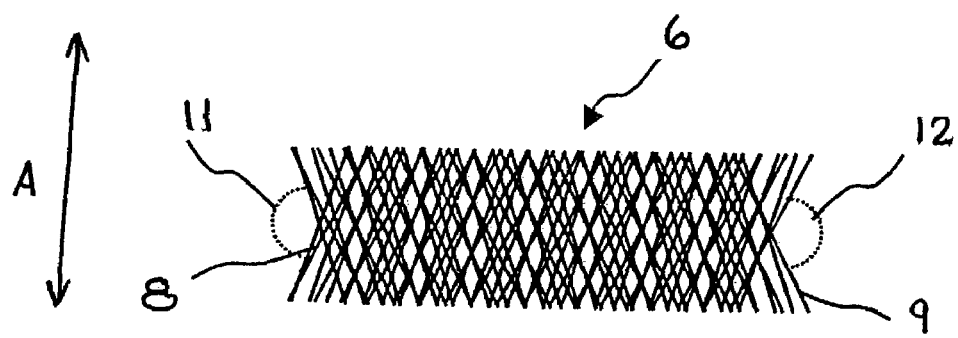
FIG. 5c shows double braid layers having two braid layers of different angles, combining FIGS. 5a and 5b, according to the present invention.

FIGS. 5a, 5b and 5c show the braid angles 11 and 12 which largely determine the relationship between radial expansion, stretchability, and axial elongation of the sheath 2. Larger braid angle 11 is more yielding in axial tension. Conversely, given a smaller braid angle 12, the structure provides higher longitudinal stiffness, providing for reduced axial elongation. As shown in FIG. 5c, a structure with two braided layers 8 and 9 of differing braid angles 11 and 12, results in resistance to the relative movement of the braids. A sheath having a smaller braid angle 12 layer circumferentially covered by a larger braid angle 11 layer provides a sheath with greater longitudinal compressive stiffness. While a sheath with a larger braid angle 11 layer circumferentially covered by a smaller braid angle 12 layer provides greater longitudinal tensile stiffness. Thus, the combination of varying braid angle layers provides the benefits of strength and longitudinal stiffness. The dissimilarity of angles of the braid layers create resistance to the relative movement longitudinally and radially.

Structural strands 13, also referred to as wire 13, used interchangeably, refers to material of a slender shape with various defined cross-sections having a cross-sectional dimension substantially less than the length of the slender shape. Such cross-sections are not limited to circular shapes, but other shapes, such as, but not limited to, rectangular, square and oval, may suitably be used. For example, the material can be in the shape of a rectangular strip. Structural strands 13 are desirably strong, biocompatible, hemocompatible and corrosion resistant. Example of materials imparting these properties include nonmetallic materials such as stiff polymer, carbon fibers, or nylon; and metallic materials such as stainless steel, gold, platinum, metal alloys such as cobalt-based alloys, alloys containing titanium, combinations thereof, or other biocompatible materials known in the art. Examples of useful cobalt-based alloys are sold under the brand names "Elgiloy," "Phynox" and "MP35N". Example of useful alloys containing titanium include a recovery metal alloy of nickel and titanium sold under the brand name "Nitinol." Other titanium alloys include titanium-zirconium-niobium alloys, and a titanium-aluminum-vanadium alloy known as "TI-6Al-4V."

Method of Making

The outer sheath 2 of the present invention can be manufactured according to the following non-limiting process. Provide materials for each layer such as PTFE for the inner layer, stainless steel for the braided layers and extruded polyetherester for the polymeric matrix layer. Provide a clean mandrel of desired diameter, place the inner layer over the mandrel assembly and secure with PTFE tape or other securing means. Next, provide the individually formed braid stocks with the desired braid angles. Cut the braided metal from the desired angle stock for each braid layer to the desired length. Slide the first braid layer over the inner layer. Slide the second braid layer over the first braid layer, in a similar manner. Tighten and secure each end of the braid layers. Continue to add the desired braid layers with varying angles. Next, cut and assemble a series of extruded polymer matrix tubes in segmented fashion over the final braided layer to vary the stiffness, hardness and thickness of the outer polymeric matrix layer. Place a fluorinated ethyl propylene (FEP) heat shrink material over the extruded outer polymer matrix layer. Heat the outer sheath assembly to activate the FEP heat-shrink and simultaneously melt the polymeric matrix layer into the interstices of the braid layers.

Allow the assembly to cool down, then remove the heat shrink by slitting it axially over its length. Dispose of used heat shrink. Pull the mandrel out of the now fused outer sheath composite. Trim both ends of the outer sheath to the specified length.

The above-described method of manufacturing the outer sheath is meant to describe one possible way to make the present invention. It is not meant to limit the method. For example, the inner or outer polymer layers may be in a liquid form and thus mandrel assembly is dipped or sprayed with the polymeric material, and an extra drying step may be necessary.

What is claimed is:

1. A sheath component of stent delivery system comprising:
    an inner tubular layer having a length and forming a polymeric luminal surface;
    at least two distinct braided layers extending the entire length of said inner tubular layer of the delivery system, said braid layers including individual braid wires, one of said at least two distinct braided layers is circumferentially braided at one braid angle over another of said at least two distinct braided layers, said another of said at least two distinct braided layers is circumferentially braided at another braid angle about said inner tubular layer, said one braid angle is different from said another braid angle; and
    a polymeric matrix encapsulating said braided layers and joining said braided layers to said inner tubular layer to form said sheath component.

2. The delivery system of claim 1, wherein said inner tubular layer is a member selected from the group consisting of fluoropolymers, polyesters, polyurethanes, polyolefins, polymethylacetates, copolymers and combinations thereof.

3. The delivery system of claim 1, wherein said inner tubular layer comprising polytetrafluoroethylene.

4. The delivery system of claim 1, wherein said polymeric luminal surface provides a lubricous surface.

5. A sheath component of an intraluminal delivery system comprising:

an elongated tubular member having a longitudinal length, said member comprising an inner layer, a first braided layer having a first braid angle circumferentially braided about the inner layer, a second braided layer having a second braid angle circumferentially braided about the first braided layer, the first braided layer and the second braided layer included individual braid wires, said first braid angle and said second braid angle are different, and a polymeric matrix layer joining together said inner layer, first braided layer and second braided layer, said first and said second braided layers extending throughout said longitudinal length of said elongated tubular member of the delivery system, wherein said first braided layer comprises a metal.

6. The delivery system of claim 5, wherein said inner layer provides a lubricious surface.

7. The delivery system of claim 5, wherein said inner layer is a member selected from the group consisting of fluoropolymers, polyesters, polyurethanes, polyolefins, polymethylacetates, copolymers and combinations thereof.

8. The delivery system of claim 5, wherein said inner layer comprising polytetrafluoroethylene.

9. The delivery system of claim 5, wherein said metal is selected from the group consisting of stainless steel, gold, platinum, metal alloys and combinations thereof.

10. The delivery system of claim 5, wherein said second braided layer comprises a metal.

11. The delivery system of claim 10, wherein said metal is selected from the group consisting of stainless steel, gold, platinum, metal alloys and combination thereof.

* * * * *